（12） United States Patent
Caruba et al.

(10) Patent No.: US 8,467,847 B2
(45) Date of Patent: Jun. 18, 2013

(54) HYBRID MR/PET SCANNER WITH PATIENT TABLE SPLIT CABLE FEED

(75) Inventors: James Frank Caruba, Bartlett, IL (US); Ralf Ladebeck, Erlangen (DE); Elmar Rummert, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 359 days.

(21) Appl. No.: 12/877,128

(22) Filed: Sep. 8, 2010

(65) Prior Publication Data

US 2012/0059242 A1 Mar. 8, 2012

(51) Int. Cl.
*A61B 5/055* (2006.01)
*A61B 6/00* (2006.01)

(52) U.S. Cl.
USPC .......................................... 600/411; 600/436

(58) Field of Classification Search
USPC ................ 600/410, 411, 415, 436; 324/318, 324/322; 250/363.03, 363.04
See application file for complete search history.

(56) References Cited

U.S. PATENT DOCUMENTS

| | | |
|---|---|---|
| 5,065,760 A | 11/1991 | Krause et al. |
| 5,666,055 A | 9/1997 | Jones et al. |
| 6,998,842 B2 | 2/2006 | Sinnema et al. |
| 7,714,582 B2 | 5/2010 | Hagen et al. |
| 7,719,271 B2 | 5/2010 | Ohsawa |
| 2007/0165786 A1 | 7/2007 | Grasser et al. |
| 2008/0045829 A1 | 2/2008 | Cho et al. |
| 2008/0177171 A1 | 7/2008 | Francesangeli et al. |
| 2009/0209844 A1 | 8/2009 | Gagnon et al. |

*Primary Examiner* — Ruth S Smith
(74) *Attorney, Agent, or Firm* — Peter Kendall (57) ABSTRACT

A hybrid magnetic resonance (MR) and positron emission tomography (PET) imaging system reduces likelihood of artifact distortion in PET images attributable to MR local coil cables and connectors in the patient table. MR local coil cables coupling the MR scanner and the MR local coil connectors are oriented so that they are outside the scanner field of view when performing PET scans.

15 Claims, 6 Drawing Sheets

HYBRID MR/PET SCANNER WITH PATIENT TABLE SPLIT CABLE FEED

BACKGROUND OF THE DISCLOSURE

1. Field of the Invention

The invention relates to hybrid combination magnetic resonance (MR) and positron emission tomography (PET) scanning systems, and more particularly to MR/PET scanning systems having patient tables with MR local coil connectors adapted for selective coupling of a so-called auxiliary MR local coil array to the table and the MR scanning portion of the hybrid scanner.

2. Description of the Prior Art

In the past, MR scanners have employed selectively auxiliary MR local coil array assemblies in order to achieve higher image resolution for imaging procedures to a patient's brain and other organ parts. A local coil assembly has been mechanically and electrically coupled to the patient table by way of local coil connectors mounted on the table. Often the local coil connectors are oriented at the head and foot of the patient table. The local coil connectors in turn were coupled to the MR scanner by local coil cables.

In order to inhibit radio frequency (RF) electromagnetic coupling of the local coil cables and an MR scanner, the cables have been shielded in metalized plastic coated faraday cages having RF traps to inhibit distortion of or interference with MR scanner data acquisition. Traditionally local coil cables have been routed down the axial centerline of an MR scanner: the location of a patient's spine during scan data acquisition. While such local coil cable routing is satisfactory for MR scanner mode of a dual mode MR/Pet scanner, it can cause unwanted image artifacts when the hybrid seamier is operated as a PET seamier. It is believed that the such artifacts are attributable to high spatial frequency attenuation and scatter from the centerline-oriented cables, shielding and associated RF trap structures within the PET scan field of view FOV).

It would not be practical to remove and reinstall MR local coil connectors, cabling and related shielding from scanners only when imaging procedures requiring MR local coils are performed, as those components are permanently installed in the patient table structure. Existing RF shielding and traps are expensive to manufacture, relatively complex to install during scanner manufacture, and they occupy considerably higher volume within the patient table than the relatively thin MR local coil cables.

There is a need in the hybrid MR/PET scanner field to minimize formation of PET image artifacts attributable to MR local coil connectors, local MR coil cables and RF related shielding/trap structure without compromising ability to utilize MR local coil structures when needed for MR scanning procedures.

There is also a need in the hybrid MR/PET scanner field to minimize volume and construction complexity of MR local coil connectors, local MR coil cables and RF related shielding/trap structure.

SUMMARY

Accordingly, an object of the invention is to reduce risk of unwanted PET image artifacts when a hybrid combination MR/PET scanner is operational in PET scanning mode for a patient, yet retain the capability of performing MR scanning procedures with patient table mounted MR local coil arrays for other patients.

Another object of the present invention is to risk of unwanted PET image artifacts when a hybrid combination MR/PET scanner is operational in PET scanning mode for a patient without removal and reinstallation of MR local coil connectors, cables and shielding.

Yet another object of the present invention is to simplify RF shielding and RF trap structures in hybrid MR/PET image scanners and space occupied by such components.

These and other objects are achieved in accordance with embodiments of the present invention by the hybrid MR/PET scanner with patient table split cable feed of the present invention that provides MR local coil array connectivity for MR scanning procedures in a manner that does not interfere with PET scanning procedures. In the present invention the local MR coil connectors, cables and related RF traps/shielding are routed to the patient table outside the PET scanning field of view (FOV) when performing PET scans.

One aspect of the present invention is directed to a hybrid PET/MR imaging system including a PET scanning system having a PET scanning field of view and an MR scanning system having an MR scanning field of view. The scanner has a patient table having front and back ends, the table translatable from a first position outside the respective scanning fields to a second position wherein at least a portion of the table mediate the ends is inside the respective scanning fields. First and second MR local coil connectors are coupled respectively to the table proximal the respective front and back ends. The connectors are adapted for connection to an MR local coil oriented on the table during an MR imaging scan. First and second MR local coil cables coupled to the MR scanning system and respectively to the first and second MR local coil connectors. Both the MR local coil cables are oriented with respect to the imaging system so that the first cable passes through the PET scanning field of view when the patient table is in the first position and is displaced outside the PET scanning field of view when the patient table is in the second position. The second cable remains outside the PET scanning field in either patient table position.

Another aspect of the present invention is directed to a hybrid PET/MR imaging system including a PET scanning system having a PET scanning field of view and an MR scanning system having an MR scanning field of view overlapping at least a portion of the PET scanning field of view. A patient table, having front and back ends, is translatable from a first position outside the respective scanning fields to a second position wherein at least a portion of the table mediate the ends is inside the respective scanning fields. First and second MR local coil connectors coupled respectively to the table proximal the respective front and back ends, adapted for connection to an MR local coil oriented on the table during an MR imaging scan. First and second MR local coil cables are coupled to the MR scanning system and respectively to the first and second MR local coil connectors. Those cables have radio frequency (RF) shielding surrounding same and are oriented with respect to the imaging system so that the first cable passes through the PET scanning field of view when the patient table is in the first position and remains outside the PET scanning field of view when the patient table is in the second position; and the second cable remains outside the PET scanning field in either patient table position.

Yet another aspect of the present invention is directed to A hybrid magnetic resonance (MR) and positron emission tomography (PET) imaging system comprising a PET scanning system having a PET scanning field of view with first and second terminating sides thereof and an MR scanning system having an MR scanning field of view. The scanner has a patient table with a front end translatable through the PET scan field of view to the second terminating side thereof, and a back end. A first local coil connector is coupled to the MR imaging system proximal the table front end, and is adapted for connection to an MR local coil oriented on the table during an MR imaging scan. A first MR local coil cable, translatable with the table, couples the MR scanning system and the first MR local coil connector. The MR local coil cable is oriented so that it is outside the PET scan field of view when the patient table front end is translated to the second terminating side thereof.

An embodiment of the present invention is also directed to a method for reducing image artifacts during a PET scan performed in a hybrid MR/PET imaging system having overlapping PET and MR scanning fields of view (FOV) with first and second terminating sides of the FOV. The scanner used to perform the method has a patient table having a front end translatable through the overlapping fields to the second terminating side of the FOV, and a back end. First and second local coil connectors are coupled to the MR imaging system and the table, adapted for connection to an MR local coil oriented on the table during an MR imaging scan. The method is performed by first mounting the first and second MR local coil connectors respectively to the table proximal the respective front and back ends. Next, the first local coil connector is coupled to the MR scanning system with a first RF-shielded MR local coil cable routed through the overlapping fields of view to the second terminating side. Next the second local coil connector is coupled to the MR scanning system with a second RF-shielded MR local coil cable routed outside the overlapping fields of view. During a PET scan the table front end is translated through the overlapping scanning fields, so that the first MR local coil connector and first MR local coil cable are on the second terminating side of the PET scan FOV.

The objects, aspects and features of embodiments of the present invention can be used severally or jointly in any combination or subcombination by those skilled in the art at their discretion.

BRIEF DESCRIPTION OF THE DRAWINGS

The teachings of embodiments of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

After considering the following description, those skilled in the art will clearly realize that the teachings of exemplary embodiments of the present invention can be readily utilized in hybrid MR/PET imaging scanners.

FIGS. 1, 2, 5 and 6 show generally a hybrid MR/PET scanner 10 of known construction and operation, having a scanner gantry 20 that incorporates scanner components necessary to acquire patient images in both the MR and PET modalities. In this exemplary hybrid scanner, the MR and PET scan fields of view (FOV), respectively 22, 24, are overlapping. For MR scanning of patient local areas of interest, such as for example a patient's cranium, a known MR local coil assembly may be attached to the patient table 30 and coupled to the MR scanner in a manner to be described in greater detail herein.

Figure 2:
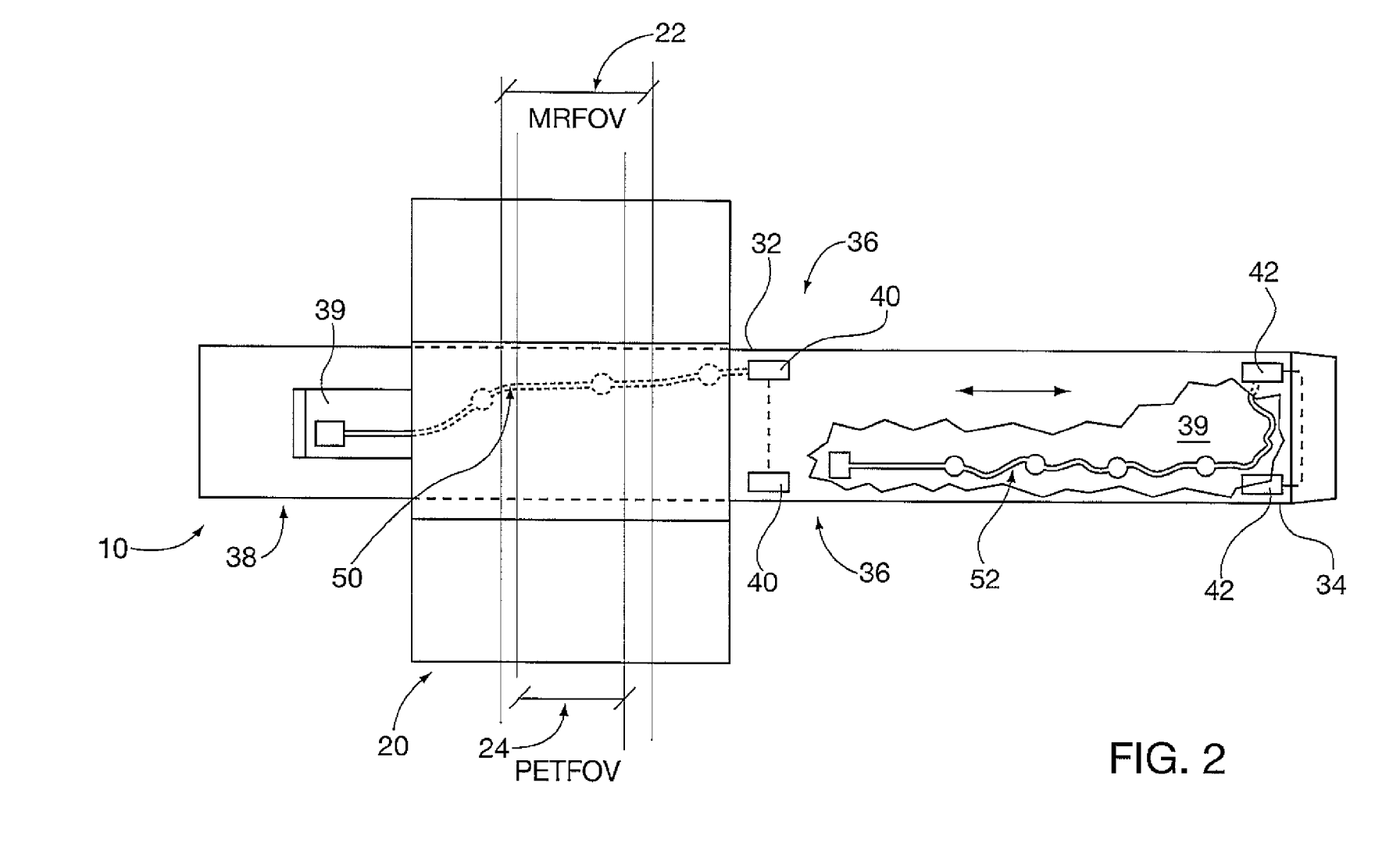
FIG. 2 is a schematic plan view of the hybrid MR/PET imaging scanner in accordance with an embodiment of the present invention.
Figure 3:
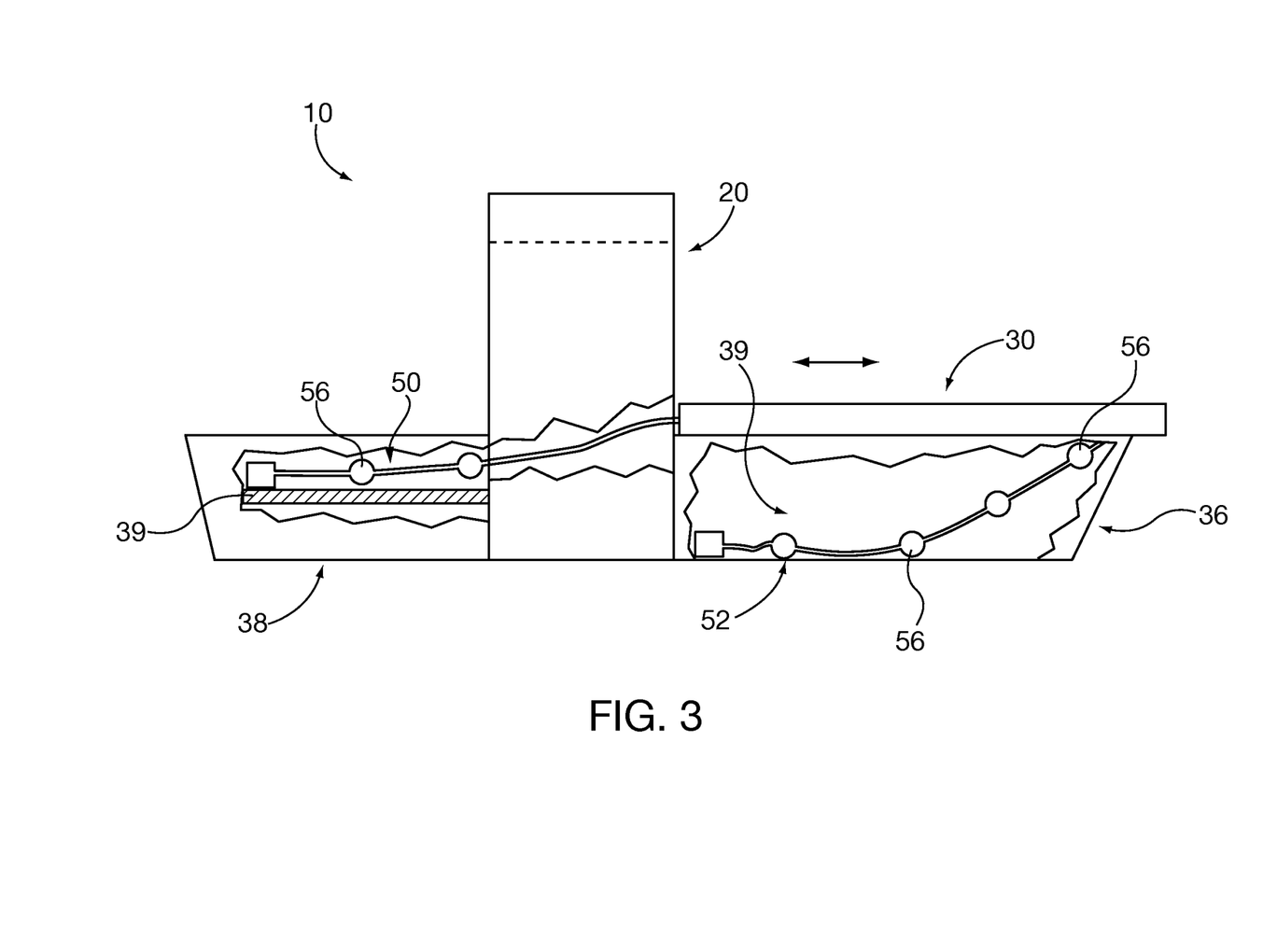
FIG. 3 is a schematic elevational view of the hybrid MR/PET imaging scanner in accordance with an embodiment of the present invention.

The patient table 30 has a front end 32 and a back end 34. Front patient table support 36 supports the patient table 30 on one side of the scanner, flanking the MR and PET FOV's 22, 24. Similarly, rear patient table support 38 supports the patient table 30 on the other side of the scanner, flanking the MR and PET FOV's 22, 24. As shown in FIGS. 2 and 3, table 30 translates from a patient loading area on the front table support 36 side of the scanner 10, where the table is entirely outside of the MR and PET FOV's 22, 24. A patient is placed on the table 30 and thereafter the table is translated so that the front 32 thereof penetrates the FOV's 22, 24, so that the portion of the patient's anatomy to be scanned is positioned in the relevant FOV for scanning. For example if it is desired to perform an MR scan on a patient's cranium utilizing a local coil assembly 26, the coil assembly is attached to the patient table 30 and positioned with the patient within the MR FOV 22.

The MR local coil assembly 26 is attached and electronically coupled to the scanner 10 by way of front local MR coil connectors 40, located in the patient table 30 proximal the front end 32. A similar set of rear local MR coil connectors 42 are provided in the patient table 30 proximal the back end 34. The respective local coil connector pairs 40, 42 are electronically coupled to the MR modality of scanner 10 by respective MR local coil cables 50, 52. The local coil cables 50, 52 have flexible RF shielding 54, such as known braided metallic shielding, with RF traps 56 selectively oriented on the cable in cooperation with the shielding.

Figure 4:
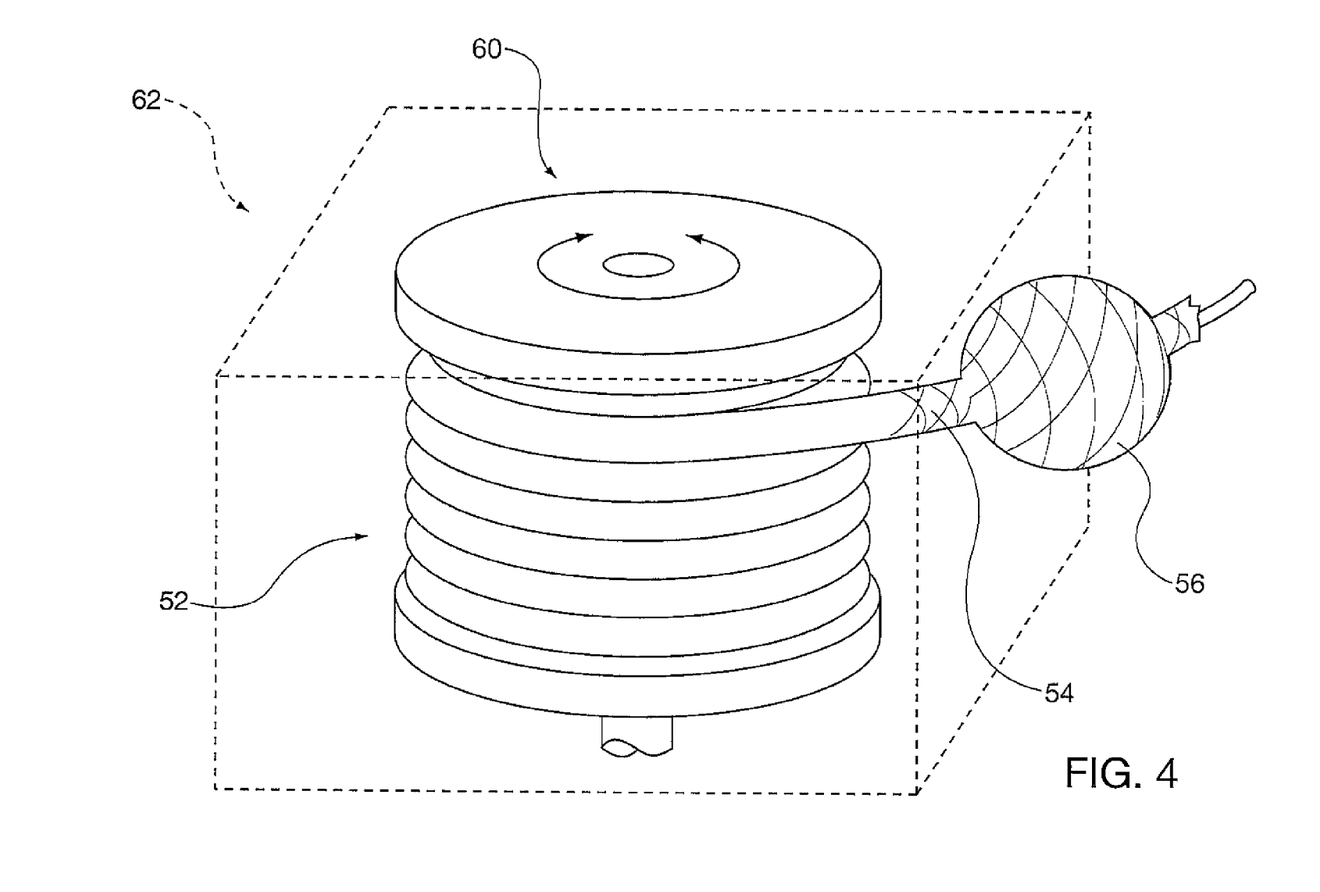
FIG. 4 is a schematic perspective view of an embodiment of a local MR coil cable reel of the hybrid MR/PET imaging scanner of the present invention.
Figure 5:
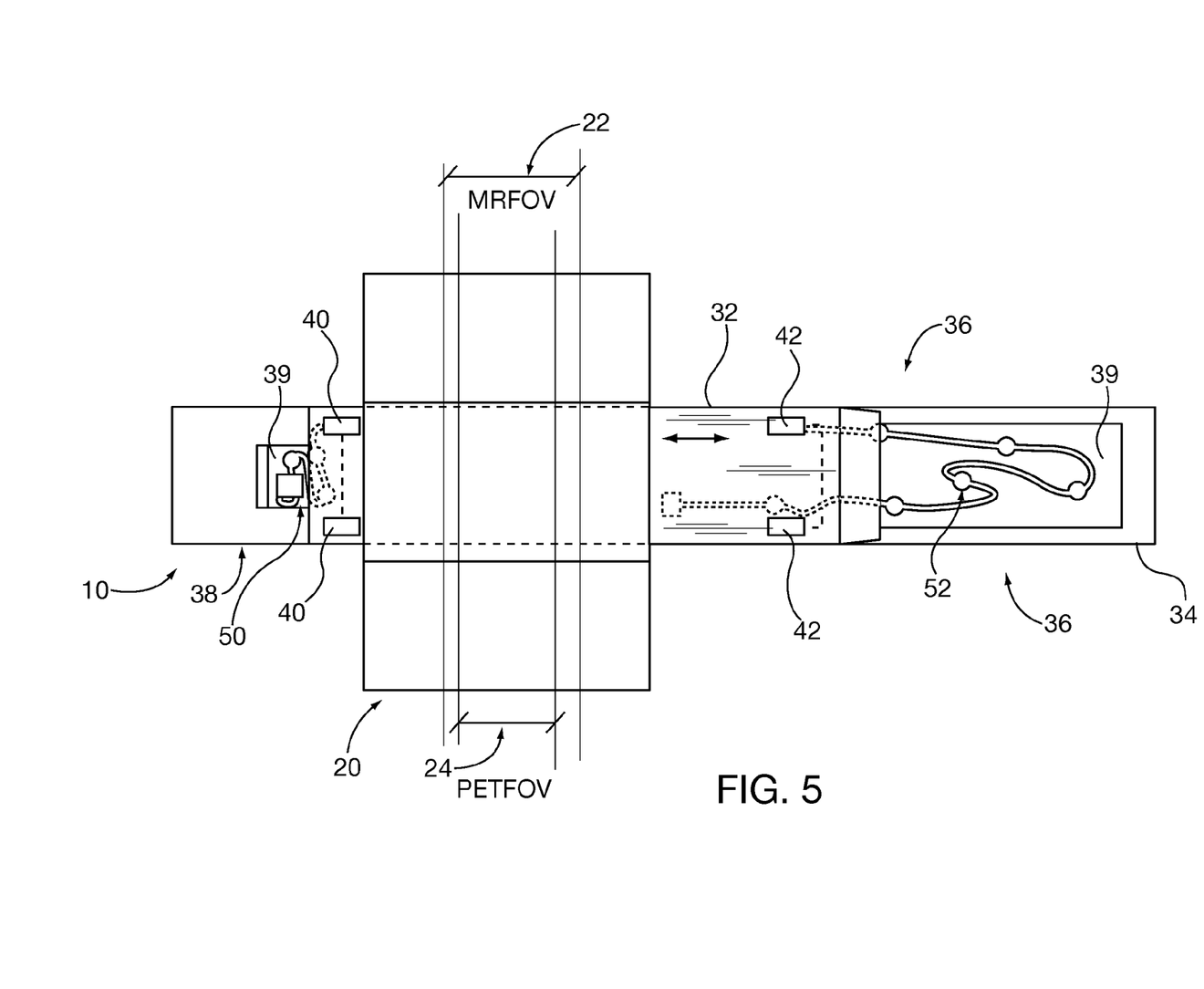
FIG. 5 is a schematic plan view of the hybrid MR/PET imaging scanner of the present invention with the patient table inserted within the scanning fields of view.
Figure 6:
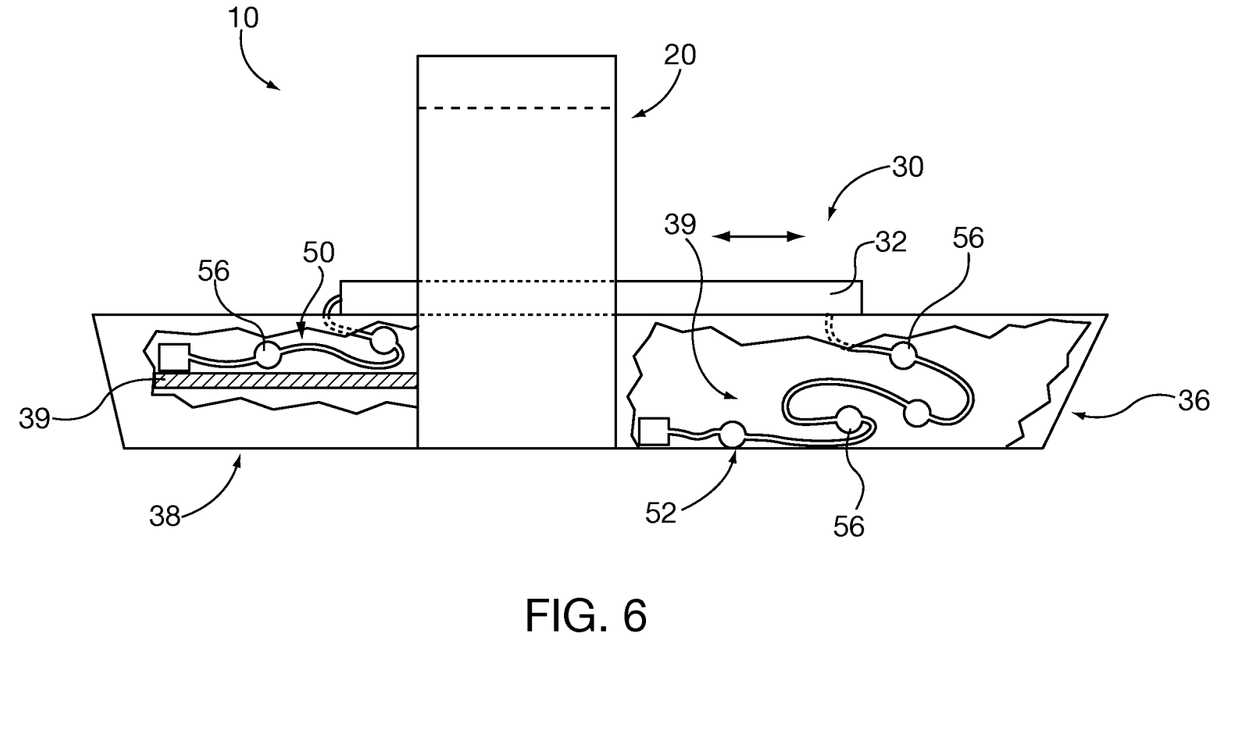
FIG. 6 is a schematic elevational view of the hybrid MR/PET imaging scanner of the present invention with the patient table inserted within the scanning fields of view.

As shown in FIGS. 1-3 and 5-6, the local coil cables 50, 52 are of sufficient length to allow the patient table 30 to translate across its entire range of motion from front table support 36 (see FIGS. 2 and 3) to rear table support 38 (see FIGS. 4 and 5). Excess cable slack can be restrained dropped within cable recesses 39. Alternatively, cable slack may be taken up by one or more cable reels 60 within an RF shielding cage 62 of known construction, and oriented in the front or rear table supports 36, 38. Any other known means of excess cable slack take-up known in the art may be utilized at the discretion of those skilled in the art.

When an MR local coil assembly 26 or other type of local coil structure is not needed to perform a patient scan, it can be removed from the patient table 30 by disconnecting from one or more of the local coil connectors 40, 42. It is intended that the MR local coil connectors 40, 42 and respective MR local coil cables 50, 52 remain in situ in the scanner 10, even when PET scans are performed.

During PET scans anything other than the patient in the PET FOV 24 has the potential for causing one or more artifacts in the acquired PET image. Therefore during a PET scan the patient table 30 is positioned in the PET FOV 24 intermediate the table front and back ends 32, 34 so that the MR local coil connectors 40, 42 are not in the FOV 24. The MR local coil cables 50, 52 are routed from the scanner 10 to their respective MR local coil connectors 40, 42 so that they do not pass through the PET scanning field of view 24 while conducting a PET scan.

Figure 1:
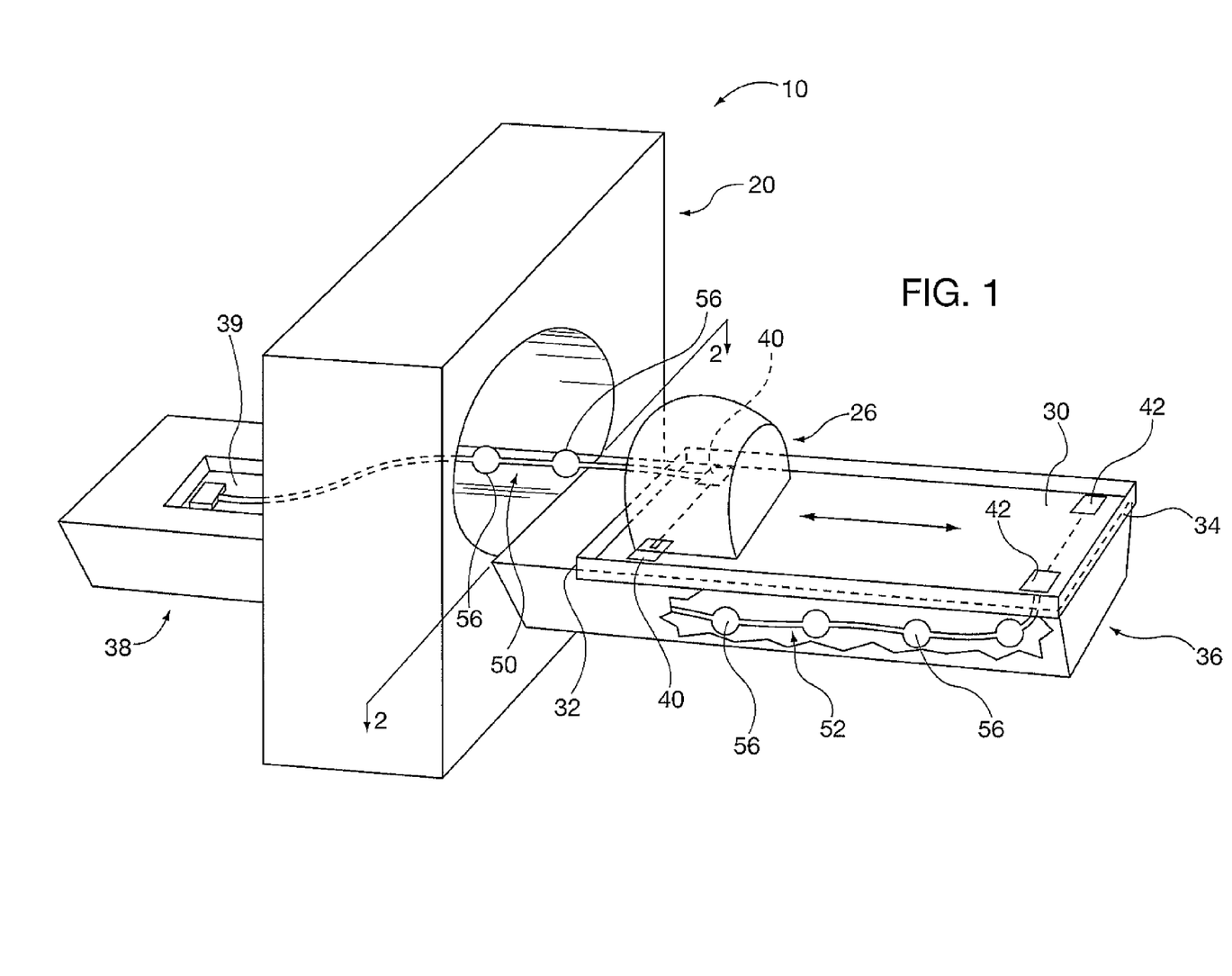
FIG. 1 is a schematic perspective view of the hybrid MR/PET imaging scanner in accordance with an embodiment of the present invention.

As is shown in FIGS. 1-3 the front local MR coil cable 50 passes through the scanner gantry 20 when the patient table 30 is in the patient loading position on the front patient table support 36 flanking side of the PET scan FOV 24. When the patient table is inserted into the gantry 20 PET scan FOV 24 the front end 32 of patient table 30 is on the rear patient table support 38 back flanking side of the PET scan FOV 24, along with the front local MR coil connectors 40 and the entire front local MR coil cable 50. In the embodiment of the present invention shown in the figures herein, the rear local MR coil connectors 42 and the associated rear local MR coil cable 52 do not enter the PET scan field of view 24 in any patient table 30 position.

As neither of the front or rear local MR coil cables 50, 52 are in the PET field of view 24 when utilizing the PET imaging modality, they do not create PET image artifacts.

Although various embodiments which incorporate the teachings of the present invention have been shown and described in detail herein, those skilled in the art can readily devise many other varied embodiments that still incorporate these teachings.

What is claimed is:

1. A hybrid magnetic resonance (MR) and positron emission tomography (PET) imaging system comprising:
   a PET scanning system having a PET scanning field of view;
   an MR scanning system having an MR scanning field of view overlapping at least a portion of the PET scanning field of view;
   a patient table having front and back ends, the table translatable from a first position outside the respective scanning fields to a second position wherein at least a portion of the table mediate the ends is inside the respective scanning fields;
   first and second MR local coil connectors coupled respectively to the table proximal the respective front and back ends outside the PET scanning field of view when the table is in the second position, the connectors adapted for connection to an MR local coil oriented on the table during an MR imaging scan;
   an MR local coil adapted for selective coupling to either of the first and second MR local coil connectors when performing an MR imaging scan; and
   first and second MR local coil cables coupled to the MR scanning system and respectively to the first and second MR local coil connectors;
   wherein both the MR local coil cables are oriented with respect to the imaging system so that:
   the first cable passes through the PET scanning field of view when the patient table is in the first position and is displaced outside the PET scanning field of view when the patient table is in the second position; and
   the second cable remains outside the PET scanning field in either patient table position.

2. The system of claim 1, wherein the MR local coil cables comprise radio frequency (RF) traps and RF shielding enveloping the cables.

3. The system of claim 1, wherein the first and second MR local coil connectors are mounted on a top surface of the table.

4. The system of claim 1, further comprising a patient table support flanking one side of the PET scanning field of view, wherein one of the MR local coil cables is retained within a recess formed therein.

5. The system of claim 1, further comprising an MR local coil cable reel for restraining cable slack during patient table translation.

6. A hybrid magnetic resonance (MR) and positron emission tomography (PET) imaging system comprising:
   a PET scanning system having a PET scanning field of view;
   an MR scanning system having an MR scanning field of view overlapping at least a portion of the PET scanning field of view;
   a patient table having front and back ends, the table translatable from a first position outside the respective scanning fields to a second position wherein at least a portion of the table mediate the ends is inside the respective scanning fields;
   first and second MR local coil connectors coupled respectively to the table proximal the respective front and back ends outside the PET scanning field of view when the table is in the second position, the connectors adapted for connection to an MR local coil oriented on the table during an MR imaging scan;
   an MR local coil adapted for selective coupling to either of the first and second MR local coil connectors when performing an MR imaging scan; and
   first and second MR local coil cables coupled to the MR scanning system and respectively to the first and second MR local coil connectors;
   the cables having radio frequency (RF) shielding surrounding same and oriented with respect to the imaging system so that:
   the first cable passes through the PET scanning field of view when the patient table is in the first position and remains outside the PET scanning field of view when the patient table is in the second position; and
   the second cable remains outside the PET scanning field in either patient table position.

7. The system of claim 6, wherein the MR local coil cables comprise radio frequency (RF) trapsalong the cables.

8. The system of claim 6, wherein the first and second MR local coil connectors are mounted on a top surface of the table.

9. The system of claim 6, further comprising a patient table support flanking one side of the PET scanning field of view, wherein one of the MR local coil cables is retained within a recess formed therein.

10. The system of claim 6, further comprising an MR local coil cable reel for restraining cable slack during patient table translation.

11. A method for reducing image artifacts during a positron emission tomography (PET) scan comprising:
   providing a hybrid magnetic resonance (MR) and positron emission tomography (PET) imaging system having: an MR local coil; overlapping PET and MR scanning fields of view with respective first and second terminating sides thereof; a patient table having a front end translatable from a first position outside the first terminating side of the PET scanning field of view to a second position outside the second terminating side thereof, and a back end; and first and second local coil connectors, the connectors adapted for connection to the MR local coil oriented on the table during an MR imaging scan and for coupling to the MR imaging system;
   mounting the first and second MR local coil connectors respectively to the table proximal the respective front and back ends so that they are outside the PET scanning field of view when the table is in the second position;

coupling the first local coil connector to the MR scanning system with a first RF-shielded MR local coil cable routed through the overlapping fields of view to the second terminating side;

coupling the second local coil connector to the MR scanning system with a second RF-shielded MR local coil cable routed outside the overlapping fields of view; and translating the table front end to the second table position through the overlapping scanning fields, so that the respective first and second MR local coil connectors and MR local coil cables are outside of the PET scanning field.

12. The method of claim 11, further comprising preventing slack in the MR local coil cables from entering the PET scanning field during PET imaging procedures.

13. The method of claim 12, wherein the slack preventing is performed with a cable reel.

14. The method of claim 12, wherein the slack preventing is performed by a retaining the cable within a recess formed in the imaging system below the table.

15. A hybrid magnetic resonance (MR) and positron emission tomography (PET) imaging system comprising:

a PET scanning system having a PET scanning field of view with first and second terminating sides thereof;

an MR scanning system having an MR scanning field of view overlapping at least a portion of the PET scanning field of view;

a patient table having:
    a front end translatable from a first position outside the first terminating side of the PET scan field of view to a second position outside the second terminating side thereof, and a back end, a first local coil connector coupled to the MR imaging system proximal the table front end outside the PET scanning field of view when the table is in the second position, the connector adapted for connection to an MR local coil oriented on the table during an MR imaging scan;

an MR local coil adapted for selective coupling to the first MR local coil connector when performing an MR imaging scan; and a first MR local coil cable, translatable with the table, coupled to the MR scanning system and the first MR local coil connector, said cable oriented so that it passes through the PET scanning field of view when the patient table is in the first position and is outside the PET scan field of view when the patient table front end is translated to the second position.

* * * * *